(12) United States Patent
Kucera et al.

(10) Patent No.: US 10,874,774 B2
(45) Date of Patent: Dec. 29, 2020

(54) ACTIVE IMPLANTABLE MEDICAL DEVICE AND METHOD OF USING AN ACTIVE IMPLANTABLE MEDICAL DEVICE

(71) Applicant: Cook Medical Technologies LLC, Bloomington, IN (US)

(72) Inventors: Lauren Kucera, Bloomington, IN (US); Ralf Spindler, Solsberry, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 36 days.

(21) Appl. No.: 16/274,745

(22) Filed: Feb. 13, 2019

(65) Prior Publication Data

US 2019/0247552 A1 Aug. 15, 2019

Related U.S. Application Data

(60) Provisional application No. 62/630,410, filed on Feb. 14, 2018.

(51) Int. Cl.
*A61F 2/90* (2013.01)
*A61L 31/16* (2006.01)
(Continued)

(52) U.S. Cl.
CPC ............... *A61L 31/16* (2013.01); *A61F 2/90* (2013.01); *A61L 31/128* (2013.01);
(Continued)

(58) Field of Classification Search
CPC ......... A61F 2/82; A61F 2/07; A61F 2002/075
(Continued)

(56) References Cited

U.S. PATENT DOCUMENTS 7,326,238 B1   2/2008   Kilpatrick et al.
8,241,653 B1   8/2012   Hossainy et al.
(Continued)

FOREIGN PATENT DOCUMENTS

WO    WO 2007/067794 A1    6/2007

OTHER PUBLICATIONS

European Search Report for corresponding European Application No. EP 19 15 7298, dated Jun. 25, 2019.
(Continued)

*Primary Examiner* — Suzette J Gherbi
(74) *Attorney, Agent, or Firm* — Brinks Gilson & Lione

(57) ABSTRACT

An active implantable medical device comprises an expandable stent, a flexible cover material positioned on at least an outer surface of the expandable stent, a nanoscale source of electrical energy embedded within the cover material, where the nanoscale source of electrical energy is mechanically activatable to produce the electrical energy, and antimicrobial particles distributed on or within a surface region of the cover material. The antimicrobial particles are electrically connected to the nanoscale source of electrical energy. When the active implantable medical device is placed in a body vessel and exposed to pressure changes and/or mechanical stresses, mechanical activation of the nanoscale source occurs, thereby enabling production of the electrical energy and powering of the antimicrobial particles.

20 Claims, 4 Drawing Sheets

(51) Int. Cl.
*A61L 31/12* (2006.01)
*H02N 1/04* (2006.01)
*H02N 2/18* (2006.01)
*B82Y 15/00* (2011.01)
*A61F 2/48* (2006.01)
*H01G 11/08* (2013.01)
*H01G 11/10* (2013.01)
*H01G 11/78* (2013.01)
*H01G 11/46* (2013.01)
*H01G 11/36* (2013.01)

(52) U.S. Cl.
CPC .............. *A61L 31/129* (2013.01); *H02N 1/04* (2013.01); *H02N 2/18* (2013.01); *A61F 2002/482* (2013.01); *A61L 2300/104* (2013.01); *A61L 2300/404* (2013.01); *A61L 2400/12* (2013.01); *A61L 2420/04* (2013.01); *B82Y 15/00* (2013.01); *H01G 11/08* (2013.01); *H01G 11/10* (2013.01); *H01G 11/36* (2013.01); *H01G 11/46* (2013.01); *H01G 11/78* (2013.01)

(58) Field of Classification Search
USPC .................................. 623/1.15–1.48
See application file for complete search history.

(56) References Cited

U.S. PATENT DOCUMENTS

| | | | |
|---|---|---|---|
| 2005/0107870 A1* | 5/2005 | Wang | A61L 31/16 623/1.44 |
| 2007/0213645 A1* | 9/2007 | Zumeris | A61L 2/24 601/46 |
| 2008/0020127 A1* | 1/2008 | Whiteford | A61L 31/08 427/2.1 |
| 2008/0021212 A1* | 1/2008 | Whiteford | C07D 259/00 540/472 |
| 2009/0005859 A1* | 1/2009 | Keilman | A61B 5/0031 623/1.42 |
| 2009/0171453 A1* | 7/2009 | Adams | A61L 31/16 623/1.43 |
| 2010/0171394 A1 | 7/2010 | Glenn et al. | |
| 2010/0318175 A1* | 12/2010 | Abarca | A61F 2/06 623/1.13 |
| 2012/0271200 A1* | 10/2012 | Martinson | A61B 5/411 600/587 |
| 2013/0245603 A1* | 9/2013 | Weber | A61M 25/104 604/506 |
| 2014/0067040 A1 | 3/2014 | Thramann | |
| 2015/0137665 A1 | 5/2015 | Imran | |
| 2016/0243026 A1* | 8/2016 | Pathak | A61K 31/37 |
| 2016/0256107 A1* | 9/2016 | Gupta | A61B 5/6862 |
| 2016/0317095 A1 | 11/2016 | Berger et al. | |
| 2017/0196478 A1* | 7/2017 | Hunter | A61B 5/6847 |
| 2017/0197085 A1 | 7/2017 | Imran | |
| 2018/0243674 A1* | 8/2018 | Gulrez | B01D 39/1623 |
| 2019/0246916 A1* | 8/2019 | Kuraguntla | A61F 2/06 |
| 2019/0247538 A1* | 8/2019 | Dehnad | A61K 33/24 |
| 2019/0255225 A1* | 8/2019 | McGrath | C23C 14/34 |
| 2019/0374213 A1* | 12/2019 | Goldsmith | A61M 1/3666 |

OTHER PUBLICATIONS

Abbaszadegan et al., "The Effect of Charge at the Surface of Silver Nanoparticles on Antimicrobial Activity against Gram-Positive and Gram-Negative Bacteria: A Preliminary Study," *Journal of Nanomaterials*, vol. 2015, Article ID 720654, 8 pages (2015).

Hobman, Jon L. et al., "Bacterial antimicrobal metal ion resistance," *Journal of Medical Microbiology*, 64 (2014) 471-497.

Hwang, Geon-Tae et al., "Self-Powered Cardiac Pacemaker Enabled by Flexible Singe Crystalline PMN-PT Piezoelectric Energy Harvester," *Advanced Materials*, 26, 28 (2014) 4880-4887.

Lv, Zhisheng et al., "Editable Supercapacitors with Customizable Stretchability Based on Mechanically Strengthened Ultralong $MnO_2$ Nanowire Composite" *Advanced Materials*, 30, 1704531 (2018) 1-9.

Park, Kwi-Il et al., "Flexible Nanocomposite Generator Made of $BaTiO_3$ Nanoparticles and Graphitic Carbons," *Advanced Materials*, 24 (2012) 2999-3004.

Wang, Zhong Lin, "Triboelectric nanogenerators as new technology and self-powered sensors—Principles, problems and perspectives," *Faraday Discussions*, 176 (2014), 447-458.

* cited by examiner

ACTIVE IMPLANTABLE MEDICAL DEVICE AND METHOD OF USING AN ACTIVE IMPLANTABLE MEDICAL DEVICE

The present patent document claims the benefit of the filing date under 35 U.S.C. 119(e) to U.S. Provisional Patent Application No. 62/630,410, which was filed on Feb. 14, 2018, and is hereby incorporated by reference in its entirety.

TECHNICAL FIELD

The present disclosure is directed generally to implantable medical devices and more particularly to implantable medical devices having power generation capabilities.

Background

In medicine, stents may be inserted in a body lumen, vessel, or duct to keep the passageway open. For example, in aortic intervention, stents can address and correct issues resulting from atheroschlerotic plaques, aneurysm or weakening of blood vessels, and arterial dissection. Currently, stents are passive devices that cannot use or generate energy to perform specific functions. Transforming stents and/or other implantable medical device from passive to active devices may open the door to new functions and/or improved efficacy.

BRIEF SUMMARY

An active implantable medical device comprises an expandable stent, a flexible cover material positioned on at least an outer surface of the expandable stent, a nanoscale source of electrical energy embedded within the cover material, where the nanoscale source of electrical energy is mechanically activatable to produce the electrical energy, and antimicrobial particles distributed on or within a surface region of the cover material. The antimicrobial particles are electrically connected to the nanoscale source of electrical energy. When the active implantable medical device is placed in a body vessel and exposed to pressure changes and/or mechanical stresses, mechanical activation of the nanoscale source occurs, thereby enabling production of the electrical energy and powering of the antimicrobial particles.

A method of using an active implantable medical device comprises inserting an active implantable medical device into a body vessel, where the active implantable medical device comprises: an expandable stent in a delivery configuration; a flexible cover material on at least an outer surface of the expandable stent; a nanoscale source of electrical energy embedded within the cover material, where the nanoscale source of electrical energy is mechanically activatable to produce the electrical energy; and antimicrobial particles distributed on or within a surface region of the cover material. The antimicrobial particles are electrically connected to the nanoscale source of electrical energy. The the active implantable medical device is positioned at a treatment site in the body vessel, and the expandable stent is expanded from the delivery configuration to a deployed configuration, such that the active implantable medical device comes into contact with the body vessel. While the expandable stent is in the deployed configuration, the active implantable medical device is subjected to pressure changes and/or mechanical stresses within the body vessel, and the nanoscale source of electrical energy experiences frictional forces and/or deforms, thereby generating electrical energy to power the antimicrobial particles.

DETAILED DESCRIPTION

Figure 1A:
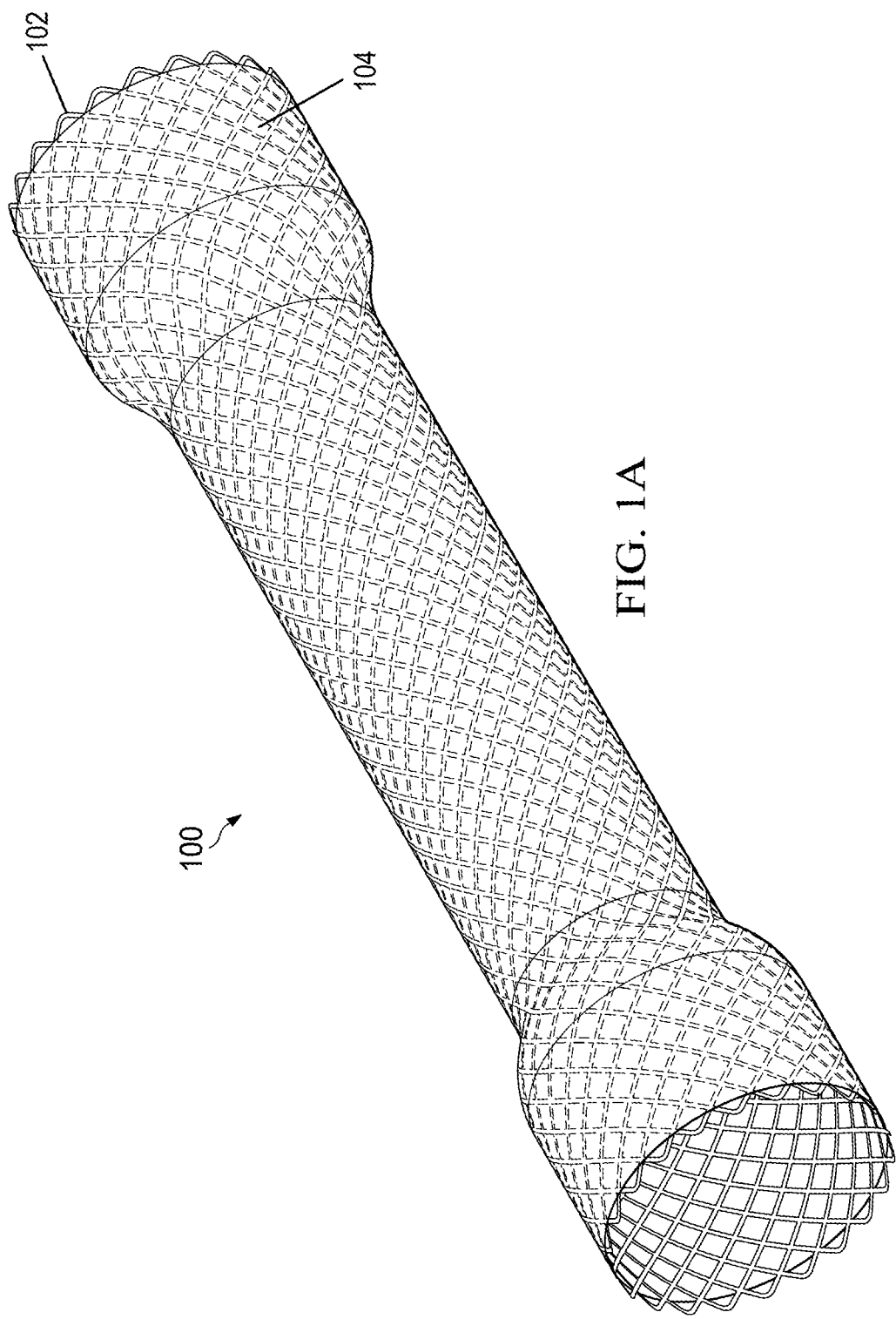
FIG. 1A shows a perspective view of an active implantable medical device according to one embodiment, where the active implantable medical device includes an expandable stent with a flexible cover material positioned on an outer surface thereof. A nanoscale source of electrical energy is embedded in the flexible cover material, and antimicrobial particles are distributed on or within a surface region of the flexible cover material in electrical contact with the nanoscale source of electrical energy, as shown schematically in FIGS. 1B and 1C.
Figure 1B:
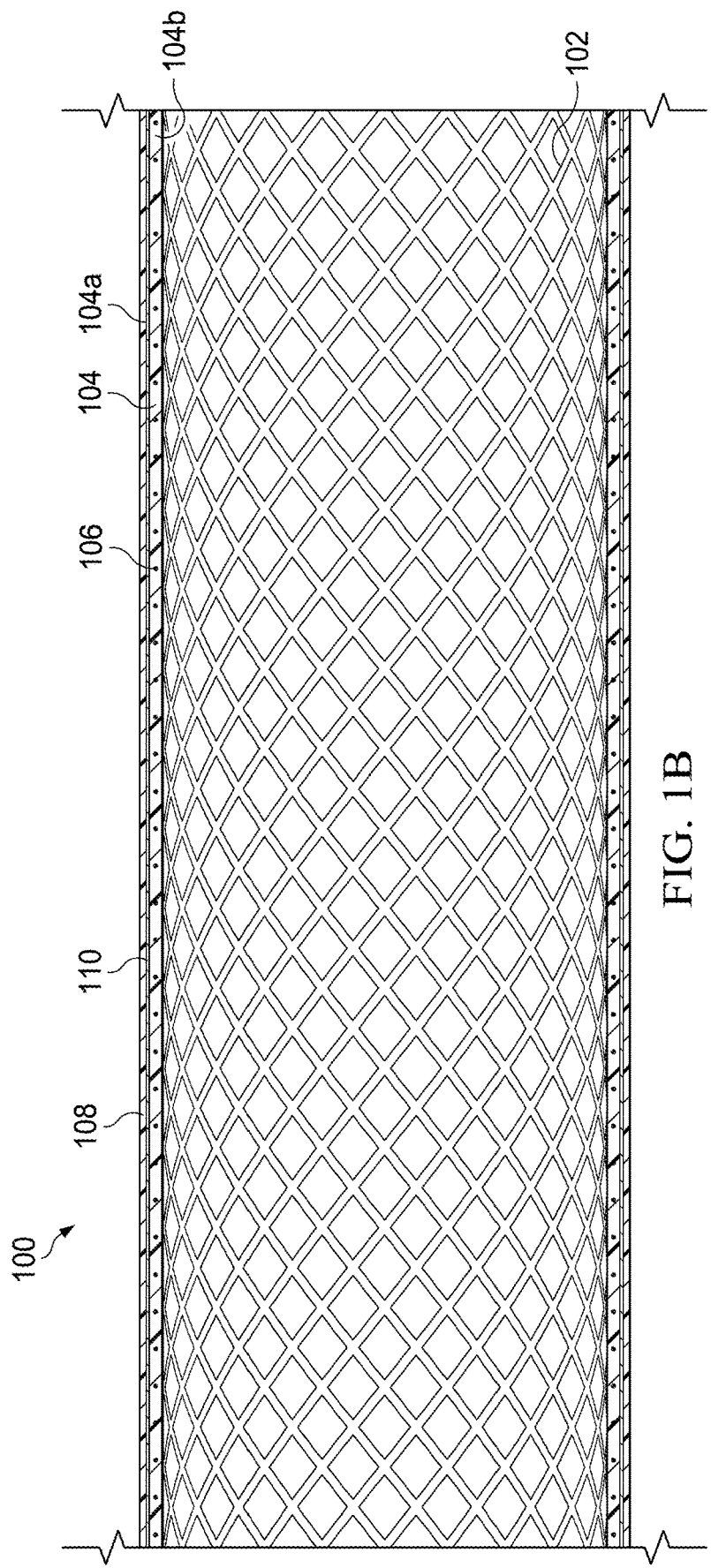
FIG. 1B shows a longitudinal sectional view of part of the active implantable medical device shown in FIG. 1A.
Figure 1C:
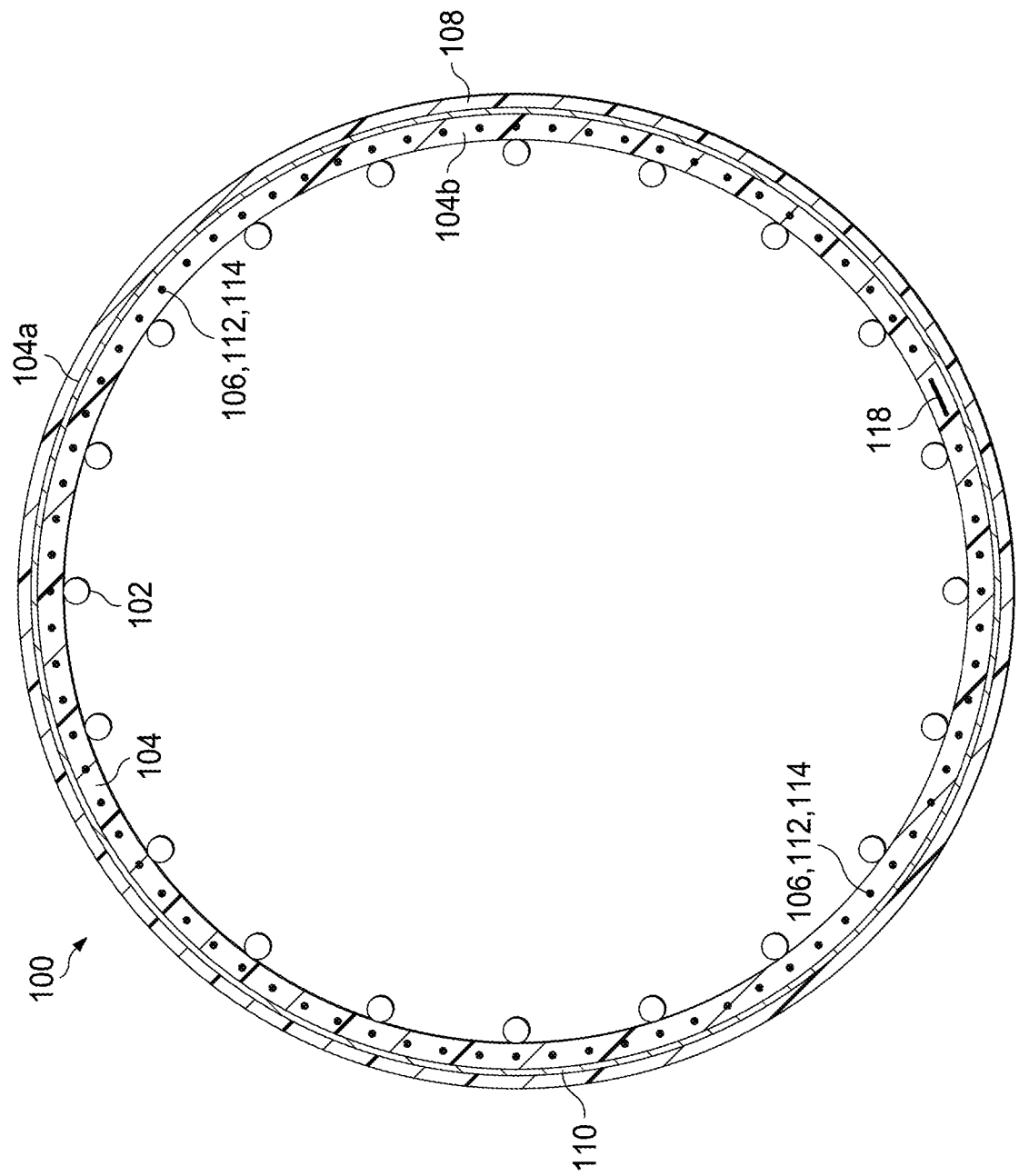
FIG. 1C shows a transverse cross-sectional view of the active implantable medical device shown in FIG. 1A.

FIGS. 1A-1C show an active implantable medical device 100 comprising an expandable stent 102 and a flexible cover material 104 positioned on an inner surface and/or an outer surface of the expandable stent 102. In other words, the flexible cover material 104 is positioned radially adjacent to the expandable stent 102, which has a generally tubular shape. A nanoscale source of electrical energy 106 is embedded within the cover material 104. The nanoscale source 106 can be mechanically activated to produce the electrical energy and thus may be described as being a mechanically-activatable nanoscale source 106. In one example, the nanoscale source of electrical energy 106 may utilize frictional forces to produce the electrical energy. In another example, the nanoscale source 106 may utilize mechanical stress (e.g., compressive, tensile, and/or shear stress) to produce the electrical energy, as discussed further below.

The active implantable medical device 100 further includes antimicrobial particles 108 distributed on or within a surface region 104a of the cover material 104. Suitable antimicrobial particles 108 may comprise silver, gold, copper, or another metal that exhibits antibacterial activity by destroying or preventing the growth of bacteria. For example, silver applied to the surface region 104a as a film (or embedded within the surface region 104a in particulate form) releases silver ions (Ag+) that have been shown to have biocidal effectiveness. The antimicrobial particles 108 are electrically connected to the nanoscale source of electrical energy 106. In one example, the active implantable medical device 100 may include a conductive layer or other conductive structure 110 between the surface region 104a and an interior portion 104b of the cover material to provide the electrical connection. When the active implantable medical device 100 is placed in a body vessel and exposed to pressure changes and/or applied stresses, mechanical activation of the nanoscale source 106 can occur, thereby enabling production of the electrical energy and powering of the antimicrobial particles 108. It has been recognized that electrical activation of the antimicrobial particles 108 can lead to an improvement in their bactericidal efficacy.

The antimicrobial particles 108 may take the form of discrete metal particles, agglomerated metal particles, and/or grains of a polycrystalline metal film (e.g., a polycrystalline silver film). The antimicrobial particles 108 may also or alternatively comprise metal particles dispersed in a polymer film, thereby forming a polymer composite on the surface region 104a. The polymer film may be electrically conductive, and may include poly(3,4-ethylenedioxythiophene) (PEDOT) or another conducting polymer. For example, poly(hydroxymethyl 3,4-ethylenedioxythiophene):polystyrene sulfonate (PEDOT-MeOH:PSS) has been shown to be a suitable conducting polymer for use with silver particles to form a polymer composite. The antimicrobial particles 108 may also or alternatively be stabilized with a suitable coupling agent, such as 3-aminopropyltriethoxysilane (APTES).

It may be beneficial for the antimicrobial particles 108 to have a high surface area-to-volume ratio to promote release of the silver (or other metal) ions. Thus, the antimicrobial particles 108 may be antimicrobial nanoparticles having an average linear size (e.g., diameter or width) in a range from about 1 nm to about 500 nm, from about 2 nm to about 200 nm, or from about 5 nm to about 100 nm. As indicated above, the antimicrobial nanoparticles 108 may take the form of discrete metal nanoparticles, agglomerated metal nanoparticles, or grains of a nanocrystalline metal film. The antimicrobial nanoparticles may be surface-stabilized as described above and may also or alternatively be distributed in a polymer film, thereby forming a polymer nanocomposite.

Figure 2:
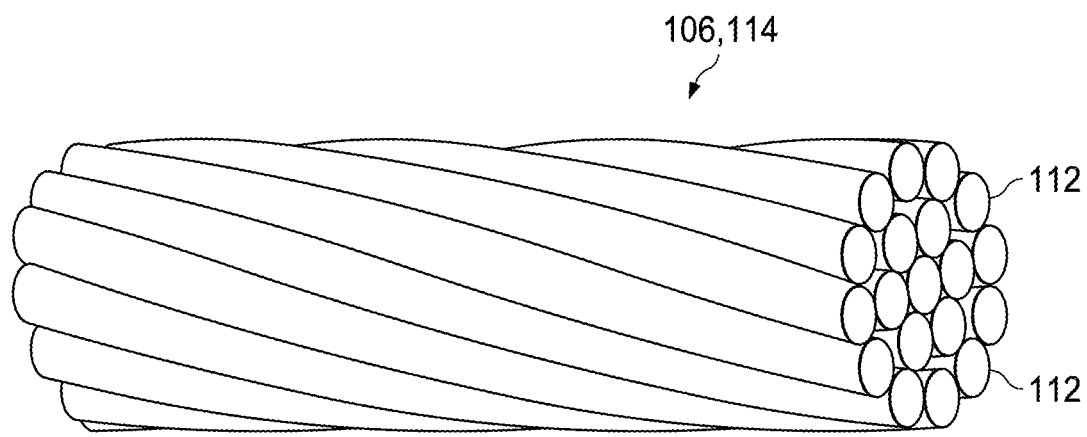
FIG. 2 shows a bundle of deformable fibers that may function as the nanoscale source of electrical energy in an active implantable medical device.
Figure 3:
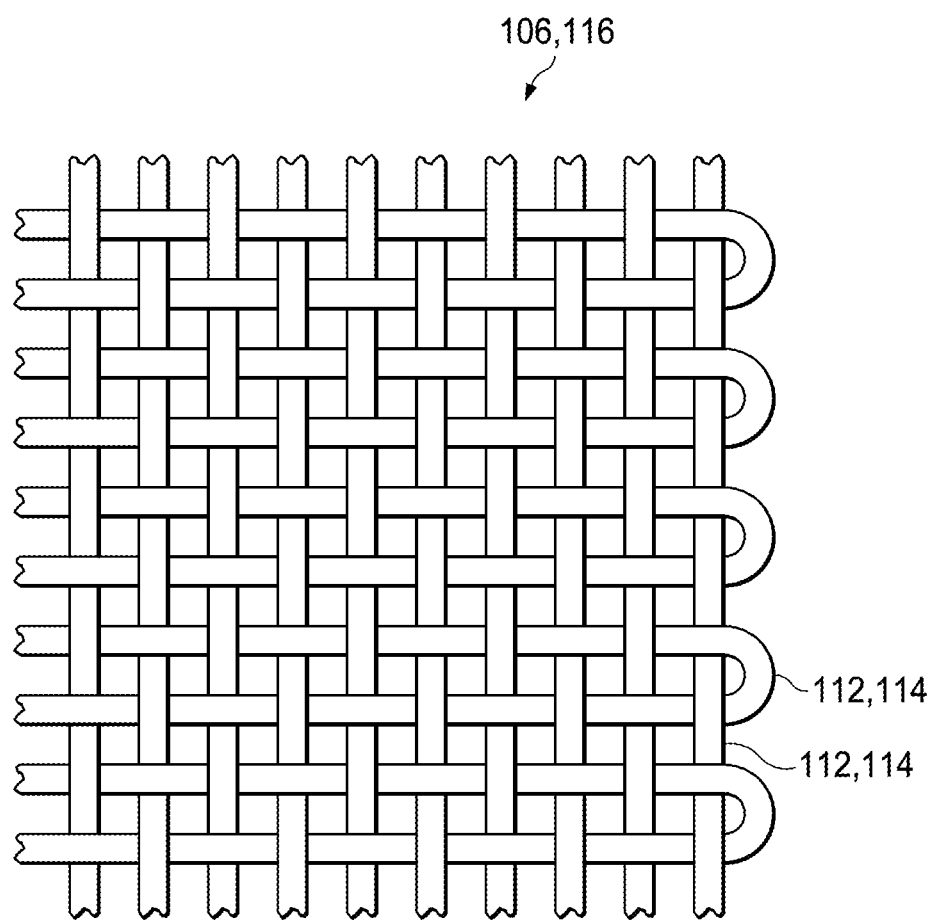
FIG. 3 shows a fabric comprising deformable fibers or bundles of deformable fibers; the fabric may be embedded in the flexible cover material of an active implantable medical device.

The nanoscale source of electrical energy 106 may comprise a plurality of deformable fibers 112 distributed within the cover material 104. Advantageously, the deformable fibers 112 may be distributed in bundles 114, as illustrated in FIG. 2, where each bundle comprises two or more deformable fibers in a twisted arrangement that may promote frictional contact during use. In one example, a fabric 116 that includes the deformable fibers 112 (or bundles 114 of the deformable fibers 112) in a woven arrangement, as shown in FIG. 3, may be embedded within the cover material 104. The deformable fibers 112 may have nanoscale dimensions, such as a width or diameter in a range from about 1 nm to about 500 nm. The length of the deformable fibers 112 may be much larger than the width or diameter.

The nanoscale source of electrical energy 106 (e.g., the deformable fibers 112) may comprise a piezoelectric material and/or a triboelectric material, where a piezoelectric material may be understood to be a material that generates electrical charge when subjected to a mechanical stress (thereby exhibiting the piezoelectric effect), and a triboelectric material may be understood to be a material that generates electrical charge when subjected to frictional contact (thereby exhibiting the triboelectric effect).

Suitable piezoelectric materials for the nanoscale source of electrical energy 106 may include, for example, carbon (e.g., graphene, graphite, carbon nanotubes), boron nitride, quartz, barium titanate, zinc oxide, lead zirconate titanate (PZT), bismuth titanate, sodium bismuth titanate, bismuth ferrite, potassium niobate, sodium niobate, sodium potassium niobate, sodium tungstate, zinc oxide, aluminum nitride, gallium nitride, indium nitride, and polyvinylidene fluoride. Suitable triboelectric materials for the nanoscale source 106 may include, for example, carbon (e.g., graphene, graphite, carbon nanotubes), nylon, aluminum, lead, nickel, copper, silver, gold, platinum, and silicon. The nanoscale source of electrical energy 106 may comprise a material that exhibits both the piezoelectric effect and the triboelectric effect.

When implanted within a body vessel, the medical device 100 is subjected to pressure changes in the vessel as well as to mechanical stresses from expansion, contraction, and/or bending of the vessel wall. Consequently, in use, the deformable fibers 112 or other nanoscale source of electrical energy 106 may deform and experience frictional forces due to abrasive contact with adjacent fibers 112 and/or the cover material 104, thereby generating electrical energy.

The flexible cover material 104 may comprise a polymer, such as a thermoplastic polyurethane, polyamide, polysiloxane (e.g., polydimethylsiloxane (PDMS)), polyolefin, polyethylene, polyethylene terephthalate (PET), or polytetrafluoroethylene (PTFE). The flexible cover material 104 may be electrically insulating and is preferably biocompatible. In some embodiments, the cover material 104 may include two or more layers (i.e., a plurality of layers), and the nanoscale source of electrical energy 106 may be embedded between adjacent layers.

It may be beneficial to store some or all of the electrical energy produced by mechanical activation of the nanoscale source 106. Thus, one or more supercapacitors 118 may be embedded within the cover material for charge storage. Each supercapacitor 118 may be electrically connected to the nanoscale source of electrical energy 106 and to the antimicrobial particles 108. In one example, the supercapacitor 118 may be fabricated from graphene ribbons, as described for example in Chen, et al. "Graphene-based fibers for supercapacitor applications," *Nanotechnology,* 27, 3 (2015). In another example, the supercapacitor 118 may include $MnO_2$ nanowires as described in Lv, et al. "Editable Supercapacitors with Customized Stretchability Based on Mechanically Strengthened Ultralong $MnO_2$ Nanowire Composite," *Adv. Mater* 30, 1704531 (2018). Such $MnO_2$ nanowires can be stretched up to 500% and are editable into different shapes and structures.

The expandable stent 102 may comprise a metal frame that is fabricated from stainless steel, a cobalt-chrome alloy, a nickel-titanium alloy, or another biocompatible alloy. The expandable stent may be self-expanding or balloon-expandable.

The active insertable medical device 100 may be fabricated using methods known in the art. The fabrication of expandable stents 102 is well known, and may entail, for example, laser machining of a metal alloy cannula or bending a number of metal alloy wires about a mandrel to obtain the desired stent geometry (e.g., a mesh or zigzag structure). Self-expanding stents formed of nickel-titanium alloys may further require a heat setting step, as known in the art, in order to impart to the stent a remembered shape and the superelastic properties required for self-expansion in the body vessel. After fabricating the stent and prior to applying the cover material, the stent may be polished (e.g., electropolished), cleaned, and/or primed as is known in the art.

The cover material 104 may be applied to the expandable stent 102 by spraying, dipping, painting, or otherwise depositing a cover material precursor, followed by drying or curing. Multiple layers may be achieved by successive passes of depositing and drying/curing. The nanoscale source of electrical energy (e.g., deformable fibers) 106 may be applied to the medical device 100 between passes in order to embed the nanoscale source 104 in the cover material 104. The conductive layer or structure(s) 110, when present, and any supercapacitors 118 may be embedded in the cover material 104 in the same way. Generally, the cover material 104 has a thickness ranging from about 0.0025 mm to about 2.5 mm. The cover material 104 may overlie both inner and outer surfaces of the stent 102, optionally covering any cells or interstices defined by the stent geometry. If desired, the cover material 104 may be selectively applied to just the outer surface of the expandable stent 102, as shown in FIGS. 1A-1C. Finally, the antimicrobial particles may be applied to or embedded in the surface region 104a of the cover material 104 in the form of discrete metal particles, agglomerated metal particles, a polymer composite including metal particles, or a polycrystalline metal film having any of the characteristics described above, such as a nanoscale particle or grain size.

To utilize the active implantable medical device 100, the expandable stent 102 may be compressed to a delivery (unexpanded) configuration and inserted into a body vessel for positioning at a treatment site. Once at the treatment site, the stent 102 may be expanded to a deployed configuration such that the medical device 100 (and in particular the antimicrobial particles at the surface region 104a) come into contact with the vessel wall. In the deployed configuration, the medical device 100 is subjected to pressure changes in the vessel as well as mechanical stress due to expansion, contraction, and/or bending of the vessel wall. Consequently, the nanoscale source of electrical energy 106 may deform and/or experience frictional forces, thereby generating electrical energy to power the antimicrobial particles while the stent 102 is deployed.

While various embodiments have been described, it will be apparent to those of ordinary skill in the art that many more embodiments and implementations are possible. Accordingly, the embodiments described herein are examples, not the only possible embodiments and implementations.

Furthermore, the advantages described above are not necessarily the only advantages, and it is not necessarily expected that all of the described advantages will be achieved with every embodiment.

What is claimed is:

1. An active implantable medical device comprising:
   an expandable stent;
   a flexible cover material positioned on at least an outer surface of the expandable stent;
   a nanoscale source of electrical energy embedded within the cover material, the nanoscale source of electrical energy comprising a plurality of deformable fibers and being mechanically activatable to produce the electrical energy; and
   antimicrobial particles distributed on or within a surface region of the cover material, the antimicrobial particles being electrically connected to the nanoscale source of electrical energy,
   wherein, when the active implantable medical device is placed in a body vessel and exposed to pressure changes and/or mechanical stresses, mechanical activation of the nanoscale source occurs, thereby enabling production of the electrical energy and powering of the antimicrobial particles.

2. The active implantable medical device of claim 1, wherein the nanoscale source of electrical energy comprises a piezoelectric material and/or a triboelectric material.

3. The active implantable medical device of claim 2, wherein the piezoelectric material is selected from the group consisting of: graphene, graphite, carbon black, carbon nanotubes, boron nitride, quartz, barium titanate, zinc oxide, lead zirconate titanate (PZT), bismuth titanate, sodium bismuth titanate, bismuth ferrite, potassium niobate, sodium niobate, sodium potassium niobate, sodium tungstate, zinc oxide, aluminum nitride, gallium nitride, indium nitride, and polyvinylidene fluoride.

4. The active implantable medical device of claim 2, wherein the triboelectric material is selected from the group consisting of: graphene, graphite, carbon black, carbon nanotubes, nylon, aluminum, lead, nickel, copper, silver, gold, platinum, and silicon.

5. The active implantable medical device of claim 1, wherein the deformable fibers are distributed in bundles, each bundle comprising two or more deformable fibers in a twisted arrangement.

6. The active implantable medical device of claim 1, wherein a fabric comprises the deformable fibers in a woven arrangement.

7. The active implantable medical device of claim 1, wherein the antimicrobial particles distributed on or within the surface region take the form of discrete metal particles, agglomerated metal particles, grains of a polycrystalline metal film, or metal particles dispersed in a polymer film.

8. The active implantable medical device of claim 1, wherein the antimicrobial particles have an average linear size in a range from about 1 nm to about 500 nm, thereby exhibiting a high surface area-to-volume ratio.

9. The active implantable medical device of claim 1, wherein the antimicrobial particles comprise a metal exhibiting antibacterial activity and selected from the group consisting of: silver, gold, and copper.

10. The active implantable medical device of claim 1, further comprising a conductive layer or other conductive structure disposed between the surface region and an interior portion of the cover material to electrically connect the antimicrobial particles and the nanoscale source of electrical energy.

11. The active implantable medical device of claim 1, wherein the flexible cover material comprises a polymer.

12. The active implantable medical device of claim 11, wherein the polymer is selected from the group consisting of: thermoplastic polyurethane, polyamide, polysiloxane (e.g., polydimethylsiloxane (PDMS)), polyolefin, polyethylene, polyethylene terephthalate (PET), or polytetrafluoroethylene (PTFE).

13. The active implantable medical device of claim 1, wherein the flexible cover material comprises a plurality of layers, and wherein the nanoscale source of electrical energy is embedded between the layers.

14. The active implantable medical device of claim 1, further comprising one or more supercapacitors embedded within the cover material for charge storage, the one or more supercapacitors being electrically connected to the nanoscale source of electrical energy and to the antimicrobial particles.

15. The active implantable medical device of claim 14, wherein the one or more supercapacitors comprise graphene ribbons or $MnO_2$ nanowires.

16. A method of using an active implantable medical device, the method comprising:
   inserting an active implantable medical device into a body vessel, the active implantable medical device comprising:
      an expandable stent in a delivery configuration;
      a flexible cover material on at least an outer surface of the expandable stent;
      a nanoscale source of electrical energy embedded within the cover material, the nanoscale source of electrical energy being mechanically activatable to produce the electrical energy; and antimicrobial particles distributed on or within a surface region of the cover material, the antimicrobial particles being electrically connected to the nanoscale source of electrical energy, positioning the active implantable medical device at a treatment site in the body vessel; and expanding the expandable stent from the delivery configuration to a deployed configuration, the active implantable medical device coming into contact with the body vessel, wherein, while the expandable stent is in the deployed configuration, the active implantable medical device is subjected to pressure changes and/or mechanical stresses within the body vessel, and the nanoscale source of electrical energy experiences frictional forces and/or deforms, thereby generating electrical energy to power the antimicrobial particles.

17. The method of claim 16, wherein the nanoscale source of electrical energy comprises a piezoelectric and/or a triboelectric material.

18. The method of claim 16, wherein the nanoscale source of electrical energy comprises a plurality of deformable fibers.

19. The method of claim 16, wherein the antimicrobial particles distributed on or within the surface region take the form of discrete metal particles, agglomerated metal particles, grains of a polycrystalline metal film, or metal particles dispersed in a polymer film.

20. An active implantable medical device comprising:

an expandable stent;

a flexible cover material positioned on at least an outer surface of the expandable stent;

a nanoscale source of electrical energy embedded within the cover material, the nanoscale source of electrical energy being mechanically activatable to produce the electrical energy; and antimicrobial particles distributed on or within an outer surface region of the cover material, the antimicrobial particles being electrically connected to the nanoscale source of electrical energy, wherein, when the active implantable medical device is placed in a body vessel and exposed to pressure changes and/or mechanical stresses, mechanical activation of the nanoscale source occurs, thereby enabling production of the electrical energy and powering of the antimicrobial particles.

* * * * *